United States Patent [19]

Kai et al.

[11] 4,113,944
[45] Sep. 12, 1978

[54] CEPHALOSPORIN-TYPE ANTIBIOTICS AND PROCESS FOR PRODUCING THE SAME

[75] Inventors: Fumio Kai, Fujisawa; Toshinori Saito, Yokohama; Shigeo Seki; Toyoaki Kawasaki, both of Tokyo, all of Japan

[73] Assignee: Meiji Seika Kaisha, Ltd., Tokyo, Japan

[21] Appl. No.: 588,555

[22] Filed: Jun. 19, 1975

[30] Foreign Application Priority Data

Jun. 20, 1974 [JP] Japan .................................. 49/69641

[51] Int. Cl.$^2$ ................. C07D 501/54; C07D 501/56; A61K 31/545
[52] U.S. Cl. ..................................... 544/27; 544/26; 424/246; 260/308 C; 260/308 R
[58] Field of Search ................. 260/243 C; 544/26, 27

[56] References Cited

U.S. PATENT DOCUMENTS

| | | | |
|---|---|---|---|
| 3,516,997 | 6/1970 | Takano et al. | 260/243 C |
| 3,641,021 | 2/1972 | Ryan | 260/243 C |
| 3,819,623 | 6/1974 | Takano et al. | 260/243 C |
| 3,985,739 | 10/1976 | Dunn et al. | 260/243 C |
| 3,989,694 | 11/1976 | Berges | 260/243 C |

FOREIGN PATENT DOCUMENTS

71/02,255  1/1971  Japan ........................... 544/26

OTHER PUBLICATIONS

Noller, Chemistry of Organic Compounds, W. B. Saunders & Co., Philadelphia (1965), pp. 597, 674, 676, 695.
Fuson, Reactions of Organic Compounds, Wiley & Sons, Inc., N.Y. (1964), pp. 664–669.

*Primary Examiner*—Donald G. Daus
*Assistant Examiner*—Diana G. Rivers
*Attorney, Agent, or Firm*—Sughrue, Rothwell, Mion, Zinn and Macpeak

[57] ABSTRACT

A cephalosporin compound represented by the formula (I) or (I')

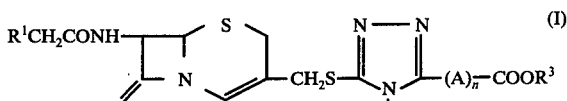

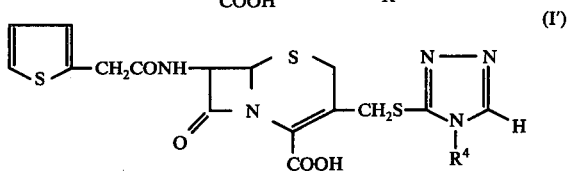

wherein $R^1$ represents a phenyl group, a 2-thienyl group or a phenoxy group; $R^2$ represents a hydrogen atom, an alkyl group having 1 to 4 carbon atoms which may be substituted with a phenyl group, an alkoxy group having 1 to 4 carbon atoms or a halogen atom, or a phenyl group which may be substituted with one or two groups selected from the group consisting of a halogen atom, a nitro group, an alkyl group having 1 to 4 carbon atoms and an alkoxy group having 1 to 4 carbon atoms; $R^3$ represents a hydrogen atom or an alkyl group having 1 to 4 carbon atoms which may be substituted with a monoalkylamino group having 1 to 4 carbon atoms in the alkyl moiety thereof, a dialkylamino group having 1 to 4 carbon atoms in each alkyl moiety thereof, a halogen atom or a phenyl group which may be substituted with one to three groups selected from the group consisting of a halogen atom, a nitro group, an alkyl group having 1 to 4 carbon atoms and an alkoxy group having 1 to 4 carbon atoms; $R^4$ represents an alkyl group having 1 to 4 carbon atoms; A has up to 15 carbon atoms and represents a straight or branched chain alkylene group, a straight or branched chain alkenylene group, a straight or branched chain alkadienylene group or a phenylene group, and $n$ is 0 or 1; or the salt thereof; and a process for preparing the same.

25 Claims, No Drawings

CEPHALOSPORIN-TYPE ANTIBIOTICS AND PROCESS FOR PRODUCING THE SAME

BACKGROUND OF THE INVENTION

1. Field Of The Invention

This invention relates to novel cephalosporin-type antibiotics having an excellent antimicrobial activity and a low toxicity and to a process for producing the same.

2. Description Of The Prior Art

Hitherto, a wide variety of cephalosporin-type antibiotics are known in the art, for example, as described in Japanese Patent Publication Nos. 17,936/64, 26,972/64, and 12,136/71. However, none of these prior art references disclose that 3-(substituted-thiomethyl)-cephalosporin-type compounds having a 1,3,4-triazole moiety substituted with a carboxylic acid ester as defined by the formula (I) described herein and 7-(2-thienylacetamido)cephalosporin-type compounds having a 1,3,4-triazole moiety as defined by the formula (I') described herein possess an excellent antimicrobial activity and a low toxicity to the host to be treated.

SUMMARY OF THE INVENTION

As a result of extensive investigations on the relationship between the structure of cephalosporin-type antibiotics and their antimicrobial activities aiming at the production of novel cephalosporin-type antibiotics having a superior antimicrobial activity and a lower toxicity than any of the known cephalosporintype antibiotics, it has now been found that novel derivatives of cephalosporin-type antibiotics can be produced by substituting the acetoxymethyl group at the 3-position of the cephem ring of cephalosporin-type compounds with a substituted mercapto group of 1,3,4-triazole compounds as hereinafter described.

Accordingly, this invention provides cephalosporin-type compounds represented by the formulae (I) and (I')

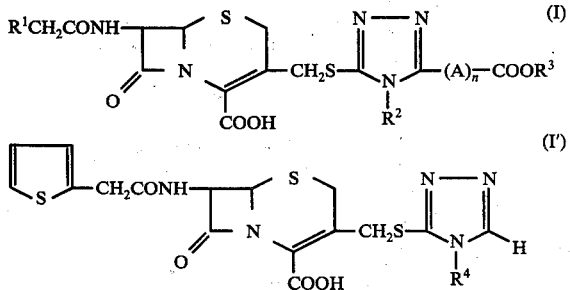

wherein $R^1$ represents a phenyl group, a 2-thienyl group or a phenoxy group; $R^2$ represents a hydrogen atom, an alkyl group having 1 to 4 carbon atoms which may be substituted with a phenyl group, an alkoxy group having 1 to 4 carbon atoms or a halogen atom, or a phenyl group which may be substituted with one or two groups selected from the group consisting of a halogen atom, a nitro group, an alkyl group having 1 to 4 carbon atoms and an alkoxy group having 1 to 4 carbon atoms; $R^3$ represents a hydrogen atom or an alkyl group having 1 to 4 carbon atoms which may be substituted with a monoalkylamino group having 1 to 4 carbon atoms in the alkyl moiety thereof, a dialkylamino group having 1 to 4 carbon atoms in each alkyl moiety thereof, a halogen atom or a phenyl group which may be substituted with one to three groups selected from the group consisting of a halogen atom, a nitro group, an alkyl group having 1 to 4 carbon atoms and an alkoxy group having 1 to 4 carbon atoms; $R^4$ represents an alkyl group having 1 to 4 carbon atoms; A has up to 15 carbon atoms and represents a straight or branched chain alkylene group, a straight or branched chain alkenylene group, a straight or branched chain alkadienylene group or a phenylene group; $R^4$ represents a straight chain or branched chain alkyl group having 1 to 4 carbon atoms and $n$ is 0 or 1; or the salt thereof.

In a second embodiment, this invention provides a process for preparing the cephalosporin-type compounds represented by the formulae (I) and (I') above comprising reacting a cephalosporin-type compound represented by the formula (II)

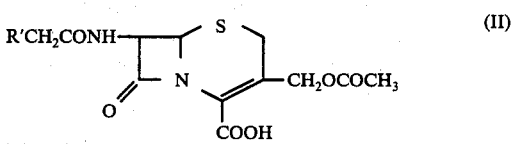

wherein $R^1$ is as defined above, with a 1,3,4-triazole compound represented by the formula (III)

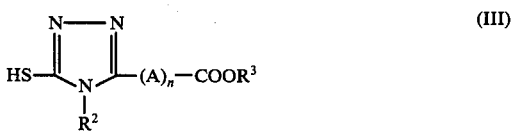

wherein $R^2$, $R^3$, A and n are as defined above, or the corresponding mercaptide compound thereof, to produce the cephalosporin-type compounds of the formula (I) and, when $n$ is 0 and $R^2$ represents an alkyl group, optionally decarboxylating the resulting compounds to cleave the —$COOR^3$ group to form the corresponding cephalosporin-type compounds of the formula (I'), and if necessary, converting the compound of the formula (I) or (I') to the salt thereof.

A further embodiment of this invention provides a process for preparing cephalosporin-type compounds represented by the formulae (I) and (I') above, which comprises reacting a 7-aminocephalosporanic acid represented by the formula (IV)

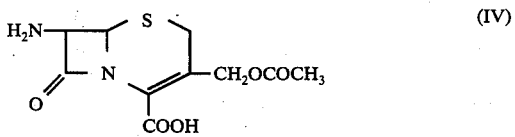

or the salt thereof, with a 1,3,4-triazole compound represented by the formula (III)

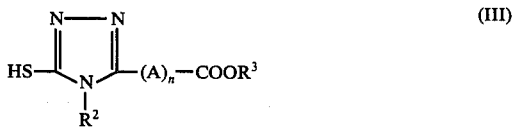

wherein $R^2$, $R^3$, A and n are as defined above, or the corresponding mercaptide compound thereof, to produce a compound represented by the formula (V)

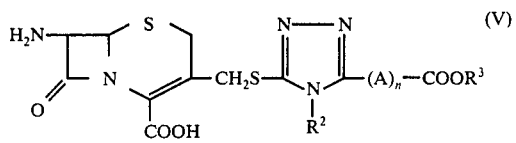

wherein $R^2$, $R^3$, A and n are as defined above, or the salt thereof, or a derivative thereof having a blocked carboxyl group, and then (1) acylating the resulting compound of the formula (V) with an active derivative of the carboxylic acid represented by the formula (VI)

$$R^1-CH_2COOH \qquad (VI)$$

wherein $R^1$ is as defined above, to produce the cephalosporin-type compounds of the formula (I) and, when n is 0, $R^1$ is a 2-thienyl group and $R^2$ is an alkyl group, optionally decarboxylating the compounds of the formula (I) to cleave the —$COOR^3$ group to form the corresponding cephalosporin-type compounds of the formula (I'), and, if necessary, converting the compound of the formula (I) or (I') to the salt thereof, or (2) when n is 0, decarboxylating the resulting compound of the formula (V) to cleave the —$COOR^3$ group to form the corresponding compounds of the formula (V')

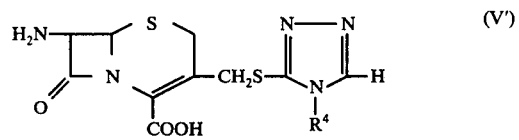

wherein $R^4$ is as defined above, and acylating the resulting compound of the formula (V') with an active derivative of the 2-thienylmethyl carboxylic acid represented by the formula (VI)

to form the cephalosporin-type compounds of the formula (I'), and, if necessary, converting the compound of the formula (I) or (I') to the salt thereof.

DETAILED DESCRIPTION OF THE INVENTION

It has further been found that the novel cephalosporin-type antibiotics having the formula (I) above exhibit a broad spectrum of antimicrobial activity against Gram-positive and Gram-negative bacteria, particularly those Gram-negative bacteria against which very few cephalosporin-type antibiotics are known to be effective, for example, *Proteus Vulgaris* and *Salmonella typhi*, and that these novel cephalosporin-type compounds are very stable with an extremely low toxicity. The present invention was completed based on the above findings.

The novel cephalosporin-type antibiotics according to the present invention can be used in the form of various salts, preferably those formed with alkali metals as is the case with known cephalosporin-type antibiotics.

These compounds when administered in a usual manner, i.e., orally, intravenously or intramuscularly as employed for antibiotic pharmaceuticals, exhibit effective activity against several infectious diseases caused by Gram-negative and Gram-positive bacteria, especially the Genera Proteus and Salmonella, at a daily dosage level of about 0.5 to 2.0 g by intravenous administration and about 1.0 to 3.0 g by oral administration for adults (about 50 ~ 70 kg)

The processes of this invention which can be employed to produce the compounds of this invention can be illustrated by the following reaction schematics. Except as otherwise indicated, $R^1$, $R^2$, $R^3$, $R^4$, A and n are as herein defined.

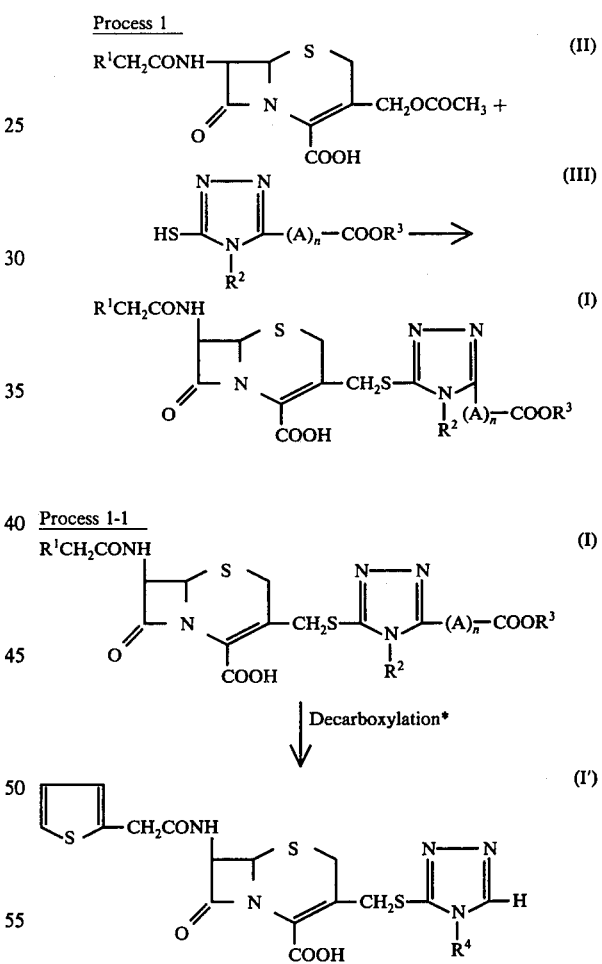

*Decarboxylation of Compound of Formula (I) wherein n is 0, $R^1$ represents a 2-thienyl group and $R^2$ represents an alkyl group (i.e., is $R^4$)

Process 2 (a)

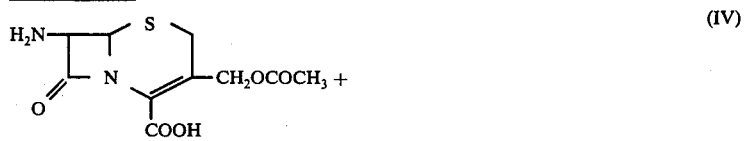

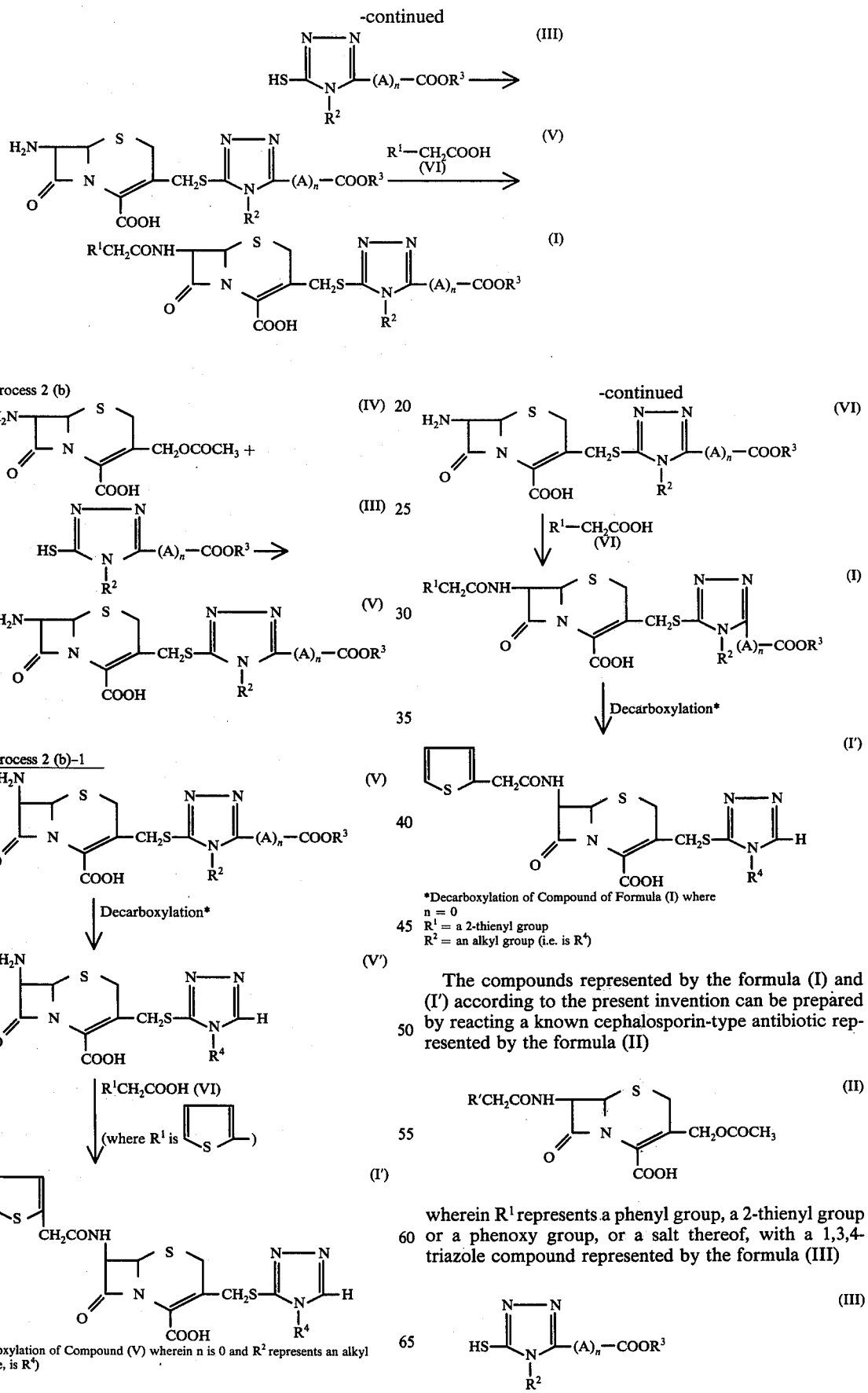
The compounds represented by the formula (I) and (I') according to the present invention can be prepared by reacting a known cephalosporin-type antibiotic represented by the formula (II)
wherein $R^1$ represents a phenyl group, a 2-thienyl group or a phenoxy group, or a salt thereof, with a 1,3,4-triazole compound represented by the formula (III)

wherein $R^2$, $R^3$, A and n are as defined above, or the corresponding mercaptide compound, to produce the cephalosporin-type compounds of the formula (I) and, when n is 0 and $R^2$ represents an alkyl group, optionally decarboxylating the resulting compounds to cleave the —$COOR^3$ group to form the corresponding cephalosporin-type compounds of the formula (I'), and, if necessary, conventing the compound of the formula (I) or (I') to the salt thereof.

The compound of the formula (II) which can be used in the present invention can be obtained by an acylation, such as a phenylacetylation as disclosed in J.D. Cocker et al., *J. Chem. Soc.*, 1965, 5015, a 2-thienylacetylation as disclosed in Japanese Patent Publication No. 26,972/64 and J. D. Cocker et al., ibid, or a phenoxyacetylation, of the primary amino group at the 7-position of a 7-aminocephalosporanic acid represented by the formula (IV)

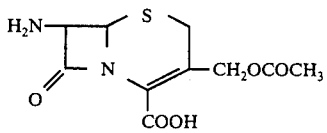

to produce, for example, 7-phenylacetamidocephalosporanic acid and 7-(2-thienylacetamido)cephalosporanic acid, etc. The starting material of the formula (IV), i.e., 7-aminocephalosporanic acid, is disclosed in Japanese Patent Publication Nos. 29,854/64 and 40,899/70 and U.S. Pat. No. 3,594,371.

Examples of the 1,3,4-triazole compounds of the formula (III) which can be used in the present invention include free carboxylic acids, esters and salts thereof, for example, 2-mercapto-1,3,4-triazole-5-carboxylic acids, such as (2-mercapto-1,3,4-triazol-5-yl)alkanecarboxylic acids, e.g., 2-(2-mercapto-1,3,4-triazol-5-yl)acetic acid, 3-(2-mercapto-1,3,4-triazol-5-yl)-propionic acid, and 2-(2-mercapto-1,3,4-triazol-5-yl)propionic acid; 1-alkyl-2-mercapto-1,3,4-triazole-5-carboxylic acids such as 2-(1-alkyl-2-mercapto-1,3,4-triazol-5-yl)acetic acids, 3-(1-alkyl-2-mercapto-1,3,4-triazol-5-yl)propionic acids, 2-(1-alkyl-2-mercapto-1,3,4-triazol-5-yl)propionic acids, 3-(1-alkyl-2-mercapto-1,3,4triazol-5-yl)acetic acids, 4-(1-alkyl-2-mercapto-1,3,4-triazol-5-yl)valerianic acids; 1-phenyl(or substituted phenyl)-2-mercapto-1,3,4-triazole-5-carboxylic acids such as 3-(2-mercapto-1,3,4-triazol-2-yl)acrylic acid, 3-(2-mercapto-1-alkyl-1,3,4-triazol-2-yl)acrylic acids, 3-[1-phenyl(or substituted phenyl)-2-mercapto-1,3,4-triazol-2-yl]acrylic acid, 2-[1-phenyl(or substituted phenyl)-2-mercapto-1,3,4-triazol-5-yl]-acetic acid, 3-[1-phenyl(or substituted phenyl)-2-mercapto-1,3,4-triazol-5-yl]propionic acids, 2-[1-phenyl(or substituted phenyl)-2-mercapto-1,3,4-triazol-5-yl]propionic acid, 3-[1-phenyl (or substituted phenyl)-2-mercapto-1,3,4-triazol-5-yl]butyric acid, 4-[1-phenyl(or substituted phenyl)-2-mercapto-1,3,4-triazol-5-yl]valerianic acid, 6-(1-methyl-2-mercapto-1,3,4-triazol-5-yl)caproic acid, 6-(2-mercapto-1,3,4-triazol-5-yl)-caproic acid, 13-(1-methyl-2-mercapto-1,3,4-triazol-5-yl)-myristic acid, 11-(2-mercapto-1,3,4-triazol-5-yl)-2-undecen-1-oic acid, 5-(2-mercapto-1,3,4-triazol-5-yl)-2,4-pentadien-1-oic acid, 7-(1-methyl-2-mercapto-1,3,4-triazol-5-yl)heptan-1-oic acid, 7-(2-mercapto-1,3,4-triazol-5-yl)heptan-1-oic acid, 7-(1-n-butyl-2-mercapto-1,3,4-triazol-5-yl)heptan-1-oic acid, 5-(1-methyl-2-mercapto-1,3,4-triazol-5-yl)-3-penten-1-oic acid, 2-(1-methyl-2-mercapto-1,3,4-triazol-5-yl)propionic acid, 2-(2-mercapto-1,3,4-triazol-5-yl)propionic acid, 3-(1-methyl-2-mercapto-1,3,4-triazol-5-yl)-2-buten-1-oic acid, 3-(2-mercapto-1,3,4-triazol-5-yl)-2-buten-1-oic acid, 2-(2-mercapto-1,3,4-triazol-5-yl)benzoic acid, 2-(1-methyl-2-mercapto-1,3,4-triazol-5-yl)benzoic acid, 3-(1-methyl-2-mercapto-1,3,4-triazol-5-yl)-benzoic acid, 3-(2-mercapto-1,3,4-triazol-5-yl)benzoic acid, 4-(2-mercapto-1,3,4-triazol-5-yl)benzoic acid, 4-(1-methyl-2-mercapto-1,3,4-triazol-5-yl)benzoic acid, and the like.

These 1,3,4-triazole compounds of the formula (III) can be prepared by cyclizing a compound of the formula (VII)

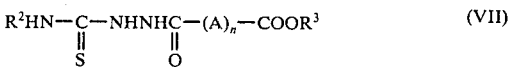

wherein $R^2$, $R^3$, A and n are as defined above. This cyclization can be carried out by treating the compound of the formula (VII) with two equivalents of an alkali such as sodium carbonate, sodium hydroxide, potassium hydroxide, triethylamine and the like at a temperature of about 25° to 100° C in an appropriate solvent such as water or a lower alcohol having 1 to 4 carbon atoms such as methanol or ethanol. When $R^3$ represents a substituent other than a hydrogen atom and only one equivalent of triethylamine or an alkali metal alkoxide is used as an alkali in a nonaqueous solvent such as an alcohol, the corresponding ester of the carboxylic acid of the formula (III) is obtained.

The corresponding carboxylic acid esters of the 1,3,4-triazole compounds of the formula (III) include lower alkyl esters such as a methyl, ethyl or propyl ester, etc., dialkylaminoalkyl esters such as a dimethylaminoethyl or diethylaminoethyl ester, etc., substituted or unsubstituted benzyl esters, alkoxyalkyl esters such as a methoxymethyl or methoxyethyl ester, etc., and the like.

In the present invention, mercaptide compounds corresponding to the 1,3,4-triazole compounds of the formula (III) can also be used. These mercaptide compounds can be obtained by reacting the —SH group of the 1,3,4-triazole compounds of the formula (III) with an organic or inorganic base. Examples of suitable bases are alkali metal hydroxides such as sodium hydroxide, potassium hydroxide, sodium carbonate, sodium bicarbonate, triethylamine, sodium methoxide, potassium methoxide and the like.

The reaction between the compounds of the formula (II) and 1,3,4-triazole compounds of the formula (III) can be usually carried out in a solution, preferably in an aqueous solution at a pH of about 5 to 9, most preferably in a solvent such as water, aqueous acetone or an aqueous lower alcohol having 1 to 4 carbon atoms at a temperature of from about 30° to 100° C and at a pH ranging from 5.5 to 8.0. Any other solvent may be employed in this reaction as long as it sufficiently dissolves the reactants and does not directly react with the reactants at the pH of the reaction mixture employed.

In the above reaction, the compounds of the formulae (II) and (III) (both of which are carboxylic acids) can generally be used partly or for the most part in the form of a salt such as an alkali metal salt dissolved in a solvent. The molar ratio of the compound of the formula (II) and the compound of the formula (III) can range from about 1:1 to 1:1.5. The conversion of part of or the most part of the compounds of the formula (II) or (III) can be conducted either by previously preparing the salts of the compounds of the formulae (II) and (III) and then dispersing the salts in a solvent for reaction or by dissolving or dispersing the compounds of the formulae (II) and (III) in the form of the free carboxylic acid in a solvent and adding an organic or inorganic base to the resulting solution or dispersion to adjust the pH to the desired value for salt formation followed by heating the solution or dispersion. Bases which can be employed in the above salt formation include various alkali metal hydroxides, alkali metal carbonates, alkali metal bicarbonates, organic amines and the like. Examples of such bases are sodium hydroxide, potassium hydroxide, sodium carbonate, potassium carbonate, sodium bicarbonate, potassium bicarbonate, sodium biphosphate, potassium biphosphate or tertiary amines, e.g., triethylamine, tributylamine and the like.

After the reaction is completed, the reaction product of the formula (I) can be isolated in a conventional manner, for example, by fractional precipitation, solvent extraction, chromatography and the like.

In this reaction, when an active or inactive carboxylic acid ester of the formula (III) is reacted whether at a relatively high pH or for a prolonged period of time, the derivative used is, as a matter of course, hydrolized in the reaction system resulting in the production of the compound of the formula (I) in which $R^3$ is a hydrogen atom. It is possible to use in this reaction an active carboxylic acid derivative of the formula (III) to increase solubility of the reactant in the solvent thereby increasing the reaction rate and the reaction yield.

The resulting compounds of the formula (I) can be appropriately separated and purified in the form of the free dicarboxylic acid or a salt of a monocarboxylic acid, a monoalkali metal, an alkaline earth metal, or a salt formed with various organic amines. If desired, those obtained in the form of a free dicarboxylic acid or a salt of a monocarboxylic acid can be converted into salts by reacting with bases usually used in a conventional manner.

Alternatively, the compounds having the formula (I) according to the present invention can be prepared by reacting a 7-aminocephalosporanic acid of the formula (IV) or the salt thereof with a 1,3,4-triazole compound of the formula (III) including the carboxylate and the corresponding mercaptide compounds in a similar manner to that hereinbefore described to obtain a compound of the formula (V)

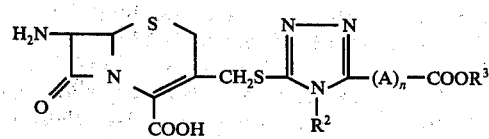

wherein $R^2$, $R^3$, A and n are as defined above, or the derivatives thereof having a blocked carboxyl group such as an ester, an acid anhydride or a mixed acid anhydride, which can then be reacted with an active derivative of the carboxylic acid represented by the formula (VI)

wherein $R^1$ represents a phenyl group, a 2-thienyl group or a phenoxy group, as an acylating agent, and, when $n$ is O, $R^1$ is a thienyl group and $R^2$ is an alkyl group, optionally the resulting compound of the formula (I) is decarboxylate to obtain the compounds of the formula (I').

When the carboxyl group in the compound of the formula (V) is blocked in the formation of the mixed acid anhdyride with a silyl ester or phosphorous acid (or the acid chloride or the ester thereof), the primary amino group in the 7-position of the compound of the formula (V) is often blocked in as the corresponding silazane-type or phosphorous amide-type. Nevertheless, the acylation of the primary amino group in the 7-position proceeds smoothly to obtain the desired compound of the formula (I).

The acylation reaction with the active carboxylic acid derivative of the formula (VI) can be carried out in an appropriate reaction medium which can be selected according to the properties of the reactants employed, for example, water, an aqueous organic solvent or an anhydrous organic solvent.

Examples of acylating agents which can be used in the above acylation, i.e., active derivatives of the carboxylic acid of the formula $R^1CH_2COOH$ (VI), are acid halides, acid anhydrides, mixed acid anhydrides with organic or inorganic acids, active esters with alcohols, phenols or thiophenols which contain electrophilic groups such as a nitro group and a halogen atom in the molecule, active amides, for example, the addition product of the carboxylic acid with a carbodiimide such as dicyclohexylcarbodiimide, carboxylic acid pseudo halides such as a carboxylic acid azide and the like.

The acylation can advantageously be effected in a well-known manner for acylating a primary amino acid with a usual acylating agent. For example, when using an acid chloride as the acylating agent, the reaction can usually be conducted by gradually adding about 1 to 3 moles of the acid chloride to the reaction system in a suitable solvent such as water, aqueous acetone, chloroform and dichloromethane in the presence of a suitable base at a temperature of 0° to about −10° C. The reaction period varies depending upon the type of the active derivative of the carboxylic acid of the formula (VI), but generally ranges from several minutes to several hours. The resulting product of the formula (I) can be isolated and purified in a conventional manner, e.g., a fractional precipitation or solvent extraction technique and, if necessary, can be converted into salts by reaction with a usual base, e.g., sodium bicarbonate or triethylamine under usual conditions.

As set forth previously, the compounds having the formulae (I) and (V) wherein n is 0, $R^1$ is a thienyl group and $R^2$ is an alkyl group can further be decarboxylated to the compounds represented by the formulae (I') and (V')

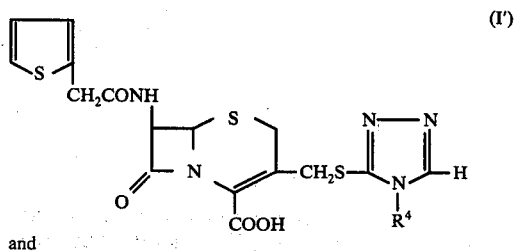

and

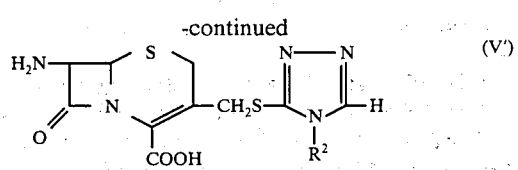

respectively, wherein $R^1$ and $R^4$ are as defined above. Of these compounds of the formulae (I') and (V'), the compounds of the formula (I') above are novel compound and it should be understood that these novel compounds and processes for producing the compounds of the formulae (I') and (V') are also included within the scope of the present invention.

The compounds of the formulae (I) or (V) wherein $n$ is 0, $R^1$ is a thienyl group and $R^2$ is an alkyl group can be selectively decarboxylated under extremely mild conditions to produce compounds of the formulae (I') and (V') in a high yield without adversely affecting moieties other than the carboxyl group or the ester group $-COOR^3$ to be cleaved.

Generally, the above decarboxylation can easily be carried out in a short period of time, e.g., a few minutes in a solvent, preferably at a pH of about 1 to about 6 and a temperature ranging from room temperature (e.g., 20°–30° C) to 100° C. In one particularly preferred embodiment, a compound of the formula (I) or (V) wherein $n$ is 0, $R^1$ is a thienyl group and $R^2$ is an alkyl group in the form of the free carboxylic acid is dissolved or suspended in an appropriate organic solvent, for example, acetone, a lower alcohol having 1 to 4 carbon atoms such as methanol, ethanol, iso-propanol and the like, or an ethereal organic solvent or water or a mixture of an organic solvent and water. The resulting solution or suspension is allowed to react at a temperature of generally from room temperature to about 60° C under reduced pressure, but other reaction conditions can be employed, if desired. For example, the reaction can easily be achieved by either employing a suitable catalyst such as active carbon or palladium-on-active carbon or allowing the free carboxylic acid to stand as a solid under reduced pressure, e.g., about 1 to 50 mmHg, or normal pressure.

Although the process for preparing the compounds of the formula (I') is disclosed herein with respect to the preparation of the novel compounds of the formula (I') through the decarboxylation of the compunds of the formula (I) wherein $n$ is O, $R^1$ is a thienyl group and $R^2$ is an alkyl group or of the compunds of the formula (V) wherein $n$ is O and $R^2$ is an alkyl group, it is to be noted that the decarboxylation is applicable in general to the compounds of the formula (I) or (V) wherein n is O whereby the group $-(A)_n-COOR^3$ can be cleaved to form the corresponding decarboxylated compounds.

The process, which has hitherto been known, for preparing the compounds represented by the formulae (I') and (V') generally comprises reacting a compound represented by the formula (VIII)

wherein $R^2$ is as defined above with a 7-acylaminocephalosphoranic acid or a 7-aminocephalosporanic acid. However, the solubility of the compounds of the formula (VIII) above in a reaction solvent or the activity thereof as a nucleophilic reagent in a substitution reaction to an acetoxy group is sometimes relatively low. In such cases, disadvantageous side reactions such as hydrolysis tend to occur during the reaction thereby causing the product to be obtained in low purity or low yield. On the other hand, the process according to the present invention starts with the compounds of the formula (II), the water-solubility of which is generally high and also the nucleophilic activity of which is high, thereby eliminating the above-described disadvantages often encountered in the conventional process. Further, since the decarboxylation reaction of the compounds of the formulae (I) and (V) wherein n is O and $R^2$ is an alkyl group proceeds extremely specifically and quantitatively, the desired compounds can be obtained in high purity and high yield. In addition, the process of the present invention is advantageous in that the preparation of the starting compounds of the formula (II) is more beneficial industrially than the starting compounds of the formula (VIII) which have been used in the conventional process. For example, when the compounds of the formula (VIII) wherein $R^2$ is a methyl group are purified by recrystallization, it is difficult to effectively separate impurities such as by-products and the like from the desired products and recrystallization should be repeated many times so as to obtain products having a satisfactory purity as a starting material and yet the resulting yield is sometimes extremely low. while, the compounds of the formula (II) wherein $R^2$ is a methyl group do not have such a disadvantage, and to the contrary, can easily be prepared in high yield and high purity.

The novel compounds of the formula (I') according to the present invention are useful as an antibiotic possessing a potent antimicrobial acitivity against Gram-positive and Gram-negative bacteria.

The novel compounds having the formula (V') can be subjected to the acylation reaction which has been hereinbefore described with respect to the preparation of the compounds of the formula (I) from the compounds of the formula (V) thereby obtaining the novel compounds of the formula (V'). Therefore, they are also useful as intermediates for the preparation of the compounds of the formula (V').

The present invention will now be illustrated by reference to the following examples, but they are not to be construed as limiting the present invention. In these examples, all parts, percentages, ratios and the like are by weight, unless otherwise indicated.

The NMR spectra of the products were analyzed using the sodium salt of 3-(trimethylsilyl)propane sulfonic acid (DSS) as an internal standard and expressed in terms of chemical shift δ (ppm) based on the signal of the methyl proton of DSS.

EXAMPLE 1

12 ml of a 0.5N aqueous solution of sodium bicarbonate was dissolved in a mixture of 836 mg of the sodium salt of 7-(2-thienylacetamido)cephalosporanic acid, 480 mg of 2-(2-mercapto-1,3,4-triazol-5-yl)acetate and 5 ml of water. The resulting solution was heated to a temperature of 62° to 65° C for 5.5 hours. After completion of the reaction, 10 ml of ice-water was added to the reaction mixture, and 8 ml of 1N HCl was slowly added thereto under ice-cooling and stirring. The precipitated white mass and filtered and washed with water. Immediately thereafter, the precipitate was pulverized with a sufficient amount of diethyl ether to obtain 810 ml of 7-(2-thienylacetamido)-3-(5-carboxymethyl-1,3,4-triazol-2-yl)thiomethyl-3-cephem-4-carboxylic acid as a white powder.

NMR Spectrum (D$_2$O—NaHCO$_3$-DSS) δ (ppm): 3.65 (singlet, 2H, —CH$_2$COONa), 3.82 (singlet, 2H, —CH$_2$CONH—), 5.0 (doublet, 1H, H at 7-position, J = 5Hz).

200 mg of the compound as obtained above was suspended in 3 ml of water, and a 0.1N aqueous solution of sodium hydroxide was added to the suspension in small portions to adjust the pH to 6.0. The resulting solution was filtered followed by drying under reduced pressure at normal temperature (i.e., about 20 ∼ 30° C) to obtain 210 mg of the sodium salt of 7-(2-thienylactamido)-3-(5-carboxymethyl-1,3,4-triazol-2-yl)thiomethyl-3-cephem-4-carboxylic acid.

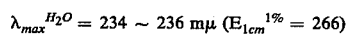

$\lambda_{max}^{H_2O} = 234 \sim 236$ mμ ($E_{1cm}^{1\%} = 266$)

500 mg of the thus-obtained 7-(2-thienylacetamido)-3-(5-carboxymethyl-1,3,4-triazol-2-yl)thiomethyl-3-cephem-4-carboxylic acid was dissolved in a mixed solvent of ethyl acetate. methanol and acetone (approximately 1:1:5 by volume). To the resulting solution was added 2 ml of a 1N acetone solution of the potassium salt of 2-ethylhexanoic acid to form a precipitate which was then filtered and washed with acetone to obtain 460 mg of the dipotassium salt of the dicarboxylic acid compound as obtained above.

The antimicrobial activity of the thus-obtained dipotassium salt was evaluated and the results obtained were as follows:

| Test Microorganism | Minimum Inhibitory Concentration (MIC) (γ/ml) |
|---|---|
| Escherichia coli | 6.25 (6.25)* |
| Proteus vulgaris | 3.13 (2.5) |
| Salmonella | 0.78 (3.13) |

*For comparison, the values in parentheses show the MIC of the sodium salt of 7-(2-thienylacetamido)cephalosporanic acid (hereinafter the same).

The ED$_{50}$ values of the above obtained compounds were determined by intravenously administering the compounds to mice suffering from infectious diseases caused by various bacteria and were compared with those obtained using known antibiotics. The results obtained are shown in the table below.

TABLE

| | ED$_{50}$ (mg/kg) | | |
|---|---|---|---|
| Test Microorganism | Compound of Example 1 | Sodium Cephalotin | Sodium Cephazoline |
| Salmonella typhi W-901-10 | 52** | 200 | |
| Proteus vulgaris* C-73-9 | 7.3*** | 14.0 | 18.5 |
| Salmonella enteritidis No.11 | 27*** | 480 | 130 |
| Staphylococcus aureus Smith S-424 | 8.5** | 19 | |

*strains produced from Cephalosporinase
**dipotassium salt
***disodium salt

Further, the acute toxicity of the same test compounds in mice (LD$_{50}$) were determined and the results obtained are shown in the table below.

TABLE

| | Compound of Example 1 (Disodium salt) | Sodium Cephalotin | Sodium Cephazoline | Cephaloridine |
|---|---|---|---|---|
| LD$_{50}$ (mg/kg) | 6300 | 5180 | 3130 | 3840 |

EXAMPLE 2

836 mg of the sodium salt of 7-(2-thineylactamido)-cephalosporanic acid was dissolved in 5 ml of water, and 520 mg of 3-(2-mercapto-1,3,4-triazol-5-yl)propionic acid was added to the solution. The resulting mixture was adjusted to a pH of 7.0 to 6.95 with 12 ml of a 0.5N aqueous solution of sodium bicarbonate and then heated to a temperature of 60° to 65° C in a nitrogen atmosphere for a period of 6 hours. After the reaction was completed, the reaction mixture was made strongly acidic by adding 8.5 ml of 1N HCl while ice-cooling with 5 ml of ice-water and stirring to precipitate white crystals, which were then filtered and washed with water. Immediately thereafter, the crystals were repeatedly washed with diethyl ether to pulverize the crystals. The resulting powder was adjusted to a pH of 6 to 6.4 with a 0.5N aqueous solution of sodium bicarbonate and filtered. The filtrate was distilled under reduced pressure at room temperature to remove water to dryness followed by drying over P$_2$O$_5$ as a drying agent for one night to produce the disodium salt of 7-(2-thienylacetamido)-3-[5-(2-carboxyethyl)-1,3,4-triazol-2-yl]thiomethyl-3-cephem-4-carboxylic acid. Yield 550 mg (50%).

NMR Spectrum (D$_2$O-DSS) δ(ppm): a symmetrical multiplet of A$_2$B$_2$ type centered at 2.81 (4H, —CH$_2$CH$_2$COONa), 3.86 (singlet, 2H, —CH$_2$COONa), 5.02 (doublet, 1H, 6-H, J = 4.5 Hz), 5.58 (doublet, 1H, 7-H, J = 4.5 Hz).

UV Absorption Spectrum: $\lambda_{max}^{H_2O} = 233 \sim 236$ mμ ($E_{1cm}^{1\%} = 288$).

The antimicrobial activity of the product was as follows:

| Test Microorganism | MIC (γ/ml) |
|---|---|
| Escherichia coli | 6.25 |
| Proteus vulgaris | 0.20 |
| Salmonella | 0.78 |

EXAMPLE 3

Following the same procedures as described in Example 2, 836 mg of a sodium salt of 7-(2-thienylacetamido)cephalosporanic acid and 560 mg of 3-(2-mercapto-1-methyl-1,3,4-triazol-5-yl)-propionic acid were reacted to obtain 660 mg of the disodium salt of 7-(2-thienylacetamido)-3-[5-(2-carboxyethyl)-1-methyl-1,3,4-triazol-2-yl]thiomethyl-3-cephem-4-carboxylic acid (yield 58 %).

NMR Spectrum (D$_2$O-DSS) δ(ppm): a symmetrical multiplet of A$_2$B$_2$ type centered at 2.82 (4H, —CH$_2$—CH$_2$—COONa), 3.87 (doublet, 2H, —CH$_2$—CONH—), 4.99 (doublet, 1H, 6-H, J = 5 Hz) and 5.53 (1H, 7-H, J = 5 Hz).

UV Absorption Spectrum: $\lambda_{max}^{H_2O} = 233 \sim 236$ mμ ($E_{1cm}^{1\%} = 288$).

The antimicrobial activity of the product was as follows:

| Test Microorganism | MIC (γ/ml) |
|---|---|
| Escherichia coli | 1.56 |
| Proteus vulgaris | 0.78 |
| Salmonella | 0.78 |

EXAMPLE 4

358 mg of the sodium salt of 7-(2-thienylacetamido)-cephalosporanic acid and 256 mg of 3-(2-mercapto-1-phenyl-1,3,4-triazol-5-yl)propionic acid were dissolved in 5 ml of water and 4.12 ml of a 0.5N aqueous solution of sodium bicarbonate. The resulting solution was heated on a water bath at 63° to 65° C in a nitrogen atmosphere for 4.5 hours. After completion of the reaction, 5 ml of ice-water and 3 ml of 1N HCl were added to the reaction mixture while ice-cooling and stirring to precipitate white crystals, which were then filtered and washed with water. Immediately thereafter, the white crystals were throughly washed with diethyl ether to obtain 440 mg of 7-(2-thienylacetamido)-3-[5-(2-carboxyethyl)-1-phenyl-1,3,4-triazol-2-yl]thiomethyl-3-cephem-4-carboxylic acid (yield, 87.5%).

The thus-obtained product was treated in the same manner as described in Example 2 to obtain the disodium salt.

NMR Spectrum ($D_2O$-DSS) δ (ppm): a symmetrical wide multiplet centered at 2.61 (4H, —$CH_2$—$CH_2$—COONa), 3.84 (singlet, 2H, —$CH_2$—CONH—), 4.92 (doublet, 1H, 6-H, J = 4.8 Hz), and 5.58 (doublet, 1H, 7-H, J = 4.8 Hz).

UV Absorption Spectrum: $\lambda_{shoulder}^{H_2O}$ = 233 m$\mu$ $^{near}$ ($E_{1cm}^{1\%}$ = 265).

The antimicrobial activity of the product was as follows:

| Test Microorganism | MIC (γ/ml) |
|---|---|
| Escherichia coli | 25 |
| Proteus vulgaris | 1.56 |
| Salmonella | 25 |

EXAMPLE 5

836 mg of the sodium salt of 7-(2-thienylacetamido)-cephalosporanic acid and 520 mg of 2-(2-mercapto-1-methyl-1,3,4-triazol-5-yl)acetic acid were slowly added to 5 ml of water and 12 ml of a 0.5N aqueous sodium bicarbonate, and the resulting solution was heated on a water bath at 60° C to 65° C in a nitrogen atmosphere for 4.5 hours. After the reaction was completed, the reaction product was worked up in the same manner as described in Example 2 to obtain 714 mg of the disodium salt of 7-(2-thienylacetamido)-3-(5-carboxymethyl-1-methyl-1,3,4-triazol-2-yl)-thiomethyl-3-cephem-4-carboxylic acid (yield, 64.5%).

NMR Spectrum ($D_2O$-DSS) δ (ppm): (3.59 (singlet, 3H, —$CH_3$), 3.78 (singlet, 2H, —$CH_2$—COONa), 3.88 (singlet, 2H, —$CH_2$—CONHO—), 5.02 (doublet, 1H, 6-H, J = 5 Hz) and 5.55 (doublet, 1H, 7-H, J = 5 Hz).

UV Absorption Spectrum $\lambda_{max}^{H_2O}$ = 233 ~ 236 m$\mu$ ($E_1^{1\%}{}_{cm}$ = 292).

The antimicorbial activity of the product was as follows:

| Test Microorganism | MIC (γ/ml) |
|---|---|
| Escherichia coli | 3.13 |
| Proteus vulgaris | 0.20 |
| Salmonella | 0.78 |

EXAMPLE 6

A solution of 418 mg of 7-(2-thienylacetamido)cephalosporanic acid and 218 mg of 2-mercapto-1,3,4-triazole-5-carboxylic acid in 20 ml of water was adjusted to a pH of 6.8 with a 0.5N aqueous solution of sodium bicarbonate, and heated at 60° to 63° in a nitrogen atmosphere for 10 hours while stirring followed by allowing to stand to cool. The reaction mixture was further cooled by adding 5 ml of ice-water and stirred whilst 1N-HCl was added to adjust the pH to 1.8. The precipitated crystals were filtered, washed with water and then dissolved in a mixture of ethyl acetate, acetone and methanol. To the resulting solution was slowly added 2 ml of a 1N solution of the potassium salt of 2-ethylhexanoic acid in acetone to produce a white precipitate, which was then filtered and washed with ethyl acetate thereby obtaining 440 mg of the disodium salt of 7-(2-thienylacetamido)-3-(5-carboxy-1,3,4-triazol-2-yl)thiomethyl-3-cephem-4-carboxylic acid (yield, 85.75%).

NMR Spectrum ($D_2O$-DSS) δ (ppm): 5.01 (doublet, 1H, 6-H, J = 4.8 Hz), 5.55 (doublet, 1H, 7-H, J = 4.8 Hz) and 3.84 (singlet, 2H, —$CH_2$—CONH—)

UV Absorption Specturm: $\lambda_{max}^{H_2O}$ = 233 ~ 236 m$\mu$ ($E_{1cm}^{1\%}$ = 304)

| Test Microorganism | MIC (γ/ml) |
|---|---|
| Escherichia coli | 6.25 |
| Proteus vulgaris | 0.20 |
| Salmonella | 3.13 |

EXAMPLE 7

In the same manner as described in Example 2, 418 mg of the sodium salt of 7-(2-thienylacetamido)cephalosporanic acid and 312 mg of 2-mercapto-1-methyl-1,3,4-triazole-5-carboxylic acid were reacted to produce 520 mg of the disodium salt of 7-(2-thienylacetamido)-3-(5-carboxy-1-methyl-1,3,4-triazol-5-yl)-thiomethyl-3-cephem-4-carboxylic acid.

NMR Spectrum ($D_2O$-DSS) δ (ppm): 3.66 (singlet, 3H, >N-$CH_3$), 5.02 (doublet, 1H, 6-H, J = 4.8 Hz) and 5.58 (doublet, 1H, 7-H, J = 4.8 Hz).

UV Absorption Spectrum: $\lambda_{max}^{H_2O}$ = 234 ~ 237 m$\mu$ ($E_{1cm}^{1\%}$ = 322).

The antimicrobial activity of the product was as follows:

| Test Microorganism | MIC (γ/ml) |
|---|---|
| Escherichia coli | 1.56 |
| Proteus vulgaris | 0.39 |
| Salmonella | 0.78 |

EXAMPLE 8

In the same manner as described in Example 2, 418 mg of the sodium salt of 7-(2-thienylacetamido)cephalosporanic acid and 265 mg of 2-mercapto-1-phenyl-1,3,4-triazole-5-carboxylic acid were reacted to obtain the disodium salt of 7-(2-thienylacetamido)-3-(5-carboxy-1-phenyl-1,3,4-triazol-5-yl)thiomethyl-3-cephem-4-carboxylic acid.

NMR Spectrum (D$_2$O-DSS) δ (ppm): 4.76 (doublet, 1H, 6-H, J = 4.6 Hz), 5.54 (doublet, 1H, 7-H, J = 4.6 Hz) and 3.80 (singlet, 2H, —CH$_2$—CONH$_{13}$).

EXAMPLES 9 TO 13

In the same manner as described in Example 2, the sodium salt of 7-(2-thienylacetamido)cephalosporanic acid was reacted with the various thiol compounds of the formula (II) as shown in Table 1 below to obtain the desired compounds of the formula (I) as shown in Table 1 below.

Table I

Compound of Formula (I)

| Example No. | R | Yield (%) | UV Absorption Spectrum $\lambda_{max}^{H_2O}$ (E$_{1cm}^{1\%}$) | NMR Spectrum (D$_2$O-DSS), δ(ppm) H at 6-position Doublet (J = Hz) | H at 7-position Doublet (J = Hz) |
|---|---|---|---|---|---|
| 9 | N—N ring with CH$_2$—COONa and phenyl | 88.4 | 236 – 237 (318) | 4.92 | 5.14 (J = 4.9Hz) |
| 10 | N—N ring with (CH$_2$)$_3$—COONa and CH$_3$ | 74.3 | 240 (275) | 5.02 | 5.58 (J = 4.7Hz) |
| 11 | N—N ring with (CH$_2$)$_3$—COONa and phenyl | 89.1 | 234 – 235 (250) | 4.88 | 5.52 (J = 4.6Hz) |
| 12 | N—N ring with CH=CH—COONa and CH$_3$ | 86.5 | 241 – 242 (332) | 5.00 | 5.53 (J = 4.8Hz) |
| 13 | N—N ring with CH=CH—COONa and phenyl | 86.3 | 233 – 234 (314) | 4.88 | 5.53 (J = 4.8Hz) |

UV Absorption Spectrum: $\lambda_{shoulder}^{H_2O}$ = 235 mμ (E$_{1cm}^{1\%}$ = 300).

The antimicrobial activity of the product was as follows:

| Test Microorganism | MIC (γ/ml) |
|---|---|
| Escherichia coli | 25 |
| Proteus vulgaris | 0.78 |
| Salmonella | 12.5 |

Example 14 to 17

5.44 g of 7-aminocephalosporanic acid was suspended in 50 ml of anhydrous chloroform, and 4 g of triethylamine dissolved in 10 ml of anhydrous chloroform was added dropwise to the resulting suspension while cooling (0° C) and stirring. To the mixture cooled to −5° C was added dropwise 3.75 g of phenoxyacetyl chloride dissolved in 20 ml of anhydrous chloroform under vigorous stirring. The stirring was further continued at −5° C for 1 hour and then at 20° C for 2 hours, and the mixture was poured into 100 ml of ice-water followed by vigorous stirring. The aqueous layer of the mixture was adjusted to a pH of 7.5, and the chloroform was distilled off at a temperature below 40° C under reduced pressure. 100 ml of ethyl acetate was added to the mixture and the aqueous layer was adjusted to pH 1.8 with dilute HCl with stirring. The ethyl acetate layer was separated and washed with water, and a 0.5N aqueous solution of sodium bicarbonate was added thereto followed by thorough stirring to adjust the pH of the aqueous layer to 6.2. The aqueous layer was then separated and lyophilized to obtain 5.0g of the sodium salt of 7-(phenoxyacetamido)cephalosporanic acid.

NMR Spectrum ($D_2O$-DSS) δ(ppm) : 2.10 (singlet, 3H, —O—$COCH_3$), 3.17 and 3.58 (AB quartet, 2H, 2—$CH_2$, $J_{AB}$=17Hz), 4.60 (singlet, 2H, —O—$CH_2$—CONH—), 5.075 (doublet, 1H, 6-H, J=4.8Hz), 5.73 (doublet, 1H, 7-H, J=4.8Hz) and 6.87–7.45 (multiplet, 5H, benzene ring proton).

In the same manner as described in Example 2, the sodium salt of 7-(phenoxyacetamido)cephalosporanic acid as obtained above was reacted with various 1,3,4-triazol compound of the formula (III) as shown in Table II below to obtain the desired compound of the formula (I) as shown in Table II below.

ml of anhydrous chloroform was then added dropwise to the mixture while thoroughly stirring. The stirring was further continued at −5° C for 1 hour and then at room temperature for 2 hours, and a cooled mixture was poured into 50 ml of ice-water. The aqueous layer of the resulting mixture was adjusted to a pH of 7.5 while thoroughly stirring, and the chloroform was distilled off at a temperature below 40° C under reduced pressure. 50 ml of ethyl acetate was added to the resulting aqueous solution and the aqueous layer was adjusted to pH 1.8 with dilute HCl with stirring. The ethyl acetate layer was separated and washed with water. A 0.5N aqueous solution of sodium carbonate was added thereto followed by thorough stirring to adjust the pH of the aqueous layer to 6.0. The aqueous layer was separated and lyophilized thereby obtaining 3.76 g of the sodium salt of 7-(phenylacetamido)cephalosporanic acid. NMR Spectrum ($D_2O$-DSS) δ(ppm) : 2.10 (singlet, 3H, —O—$COCH_3$), 3.31 and 3.68 (AB quartet, 2H, 2-$CH_2$, $J_{AB}$= 18Hz), 3.71 (singlet, 2H, $C_6H_5$—$CH_2$—CONH), 5.10 (doublet, 1H, 6-H, J=4.7Hz), 5.65 (doublet, 1H, 7-H, J=4.7Hz), 7.42 (singlet, 5H, benzene ring proton) and 4.95 and 4.71 (doublet, 2H, 3-$CH_2$O, J=13Hz).

In the same manner as described in Example 2, the sodium salt of 7-(phenylacetamido)cephalosporanic acid as obtained above was reacted with the various 1,3,4-triazole compounds as shown in Table III below to obtain the desired compounds of the formula (I) as shown in Table III below.

Table II

Compound of Formula (I)

| Example No. | R | Yield (%) | UV Absorption Spectrum $\lambda_{max}^{H_2O}$ (mμ) ($E_{1\,cm}^{1\%}$) | NMR Spectrum ($D_2O$-DSS), δ(ppm) H at 6-position Doublet (J = Hz) | H at 7-position Doublet (J = Hz) |
|---|---|---|---|---|---|
| 14 | N——N, N-H, —$CH_2$—COONa | 81.0 | 267 – 268 mμ (198) | 5.05 (J = 4.8Hz) | 5.63 (J = 4.8Hz) |
| 15 | N——N, N-$CH_3$, —$CH_2$—COONa | 77.0 | 262 mμ (192), 267 – 268 mμ | 5.05 (J = 4.8Hz) | 5.635 (J = 4.8Hz) |
| 16 | N——N, N-H, —$(CH_2)_2$—COONa | 73.5 | 264 mμ (180), 267 – 268 mμ (181) | 5.08 (J = 4.7Hz) | 5.70 (J = 4.7Hz) |
| 17 | N——N, N-$CH_3$, —$(CH_2)_2$—COONa | 43.4 | 249.5 mμ (205) | 5.03 (J = 4.8Hz) | 5.61 (J = 4.8Hz) |

Examples 18 to 21

2.72 g of 7-aminocephalosporanic acid was suspended in 30 ml of anhydrous chloroform, and the suspension was cooled to 0° C. 2.20 g of triethylamine was added to the suspension while stirring followed by cooling to −5° C. 1.85 g of phenylacetate chloride dissolved in 10

Table III

Compound of Formula (I)

[Structure: phenyl-CH₂CONH-cephem with CH₂SR at 3-position and COONa]

| Example No. | R | Yield (%) | UV Absorption Spectrum $\lambda_{max}^{H_2O}$ (mμ) ($E_{1cm}^{1\%}$) | NMR Spectrum (D₂O-DSS), δ(ppm) H at 6-position Doublet (J = Hz) | H at 7-position Doublet (J = Hz) |
|---|---|---|---|---|---|
| 18 | [triazole]-CH₂COONa (NH) | 84.9 | 240 mμ | 5.02 (J = 5.0) | 5.61 (J = 5.0) |
| 19 | [triazole]-CH₂COONa (N-CH₃) | 50.0 | 242 | 5.03 (J = 4.6) | 5.57 (J = 4.6) |
| 20 | [triazole]-(CH₂)₂-COONa (NH) | 90.9 | 240 mμ (218) | 5.00 (J = 4.9) | 5.60 (J = 4.9) |
| 21 | [triazole]-(CH₂)₂-COONa (N-CH₃) | 44.7 | 241 mμ | 5.03 (J = 4.9) | 5.56 (J = 4.9) |

Example 22

2 mg of N—HCl was added dropwise to 4 mg of an aqueous solution containing 539 mg of the disodium salt of 7-(2-thienylacetamido)-3-(2-carboxy-1-methyl-1,3,4-triazol-5-yl)thiomethyl-3-cephem-4-carboxylic acid prepared as described in Example 7 while ice-cooling and stirring. The white precipitate thus formed was filtered, washed with a small amount of water, and immediately thereafter dissolved in 4 ml of acetone. To the resulting solution was added a small amount of activated carbon, and the mixture was stirred for a while followed by filtration. The filtrate was distilled at a temperature below 30° C under reduced pressure to remove the solvent, and the residue was dissolved in ethanol. The resulting solution was adjusted to a pH of 6 with a 0.5N aqueous solution of sodium bicarbonate and the then concentrated at a temperature below 30° C and then ethanol was added to precipitate the sodium salt of 7-(2-thienylacetamide)-3-(1-methyl-1,3,4-triazol-5-yl)thiomethyl-3-cephem-4-carboxylic acid. The precipitate thus obtained was cooled sufficiently, filtered and washed with ethanol to obtain 403 mg of the product (yield, 85%). 20 mg of the desired product was further recovered from the mother liquor. The overall yield was found to be 89.5%. NMR Spectrum (D₂O-DSS) δ(ppm) : 3.70 (singlet, 3H, N—CH₃), 3.88 (singlet, 2H, —CH₂—(CONH—), 5.02 (doublet,1H, 6-H, J=5.0Hz), 5.56 (doublet, 1H, 7-H, J=5.0Hz) and 8.50 (singlet, 1H, triazole ring proton).

The antimicrobial activity of the product was as follows:

| Test Microorganism | MIC (γ/ml) |
|---|---|
| Escherichia coli | 6.25 |
| Proteus vulgaris | 50 |
| Salmonella | 1.56 |
| Staphylococcus aureaus | 0.78 |
| Pseudomonas aeruginose | 1.56 |
| Kurebusiera pneumonia | 0.78 |

EXAMPLE 23 In the same manner as described in Example 22, 412 mg of the sodium salt of 7-(2-thienylacetamido)-3-(1,3,4-triazol-5-yl)thiomethyl-3-cephem-4-carboxylic acid was obtained starting with 525 mg of the disodium salt of 7-(2-thienylacetamide)-3-(2-carboxyl-1,3,4-triazol-5-yl)thiomethyl-3-cephem-4-carboxylic acid prepared as described in Example 6 (yield, 90%).

NMR Spectrum (D₂O-DSS) δ(ppm) : 3.81 (singlet, 2H, —CH₂—CONH—), 4.04 (broad singlet, 2H, —CH₂S—), 4.96 (doublet, 1H, 6-H, J=4.8Hz), 5.525 (doublet, 1H, 7-H, J=4.8Hz) and 8.22 (singlet, 1H, triazole ring proton).

The antimicrobial activity was as follows:

| Test Microorganism | MIC (γ/mg) |
|---|---|
| Escherichia coli | 12.5 |
| Proteus vulgaris | 25 |
| Salmonella | 6.25 |
| Staphylococcus aureaus | 0.20 |

Example 24

In the same manner as described in Example 22, 505 mg of the sodium salt of 7-(2-thienylacetamide)-3-(1-phenyl-1,3,4-triazol-5-yl)thiomethyl-3-cephem-4-carboxylic acid was obtained starting with 602 mg of the disodium salt of 7-(2-thienylacetamido)-3-(2-carboxy-1-phenyl-1,3,4-triazol-5-yl)-thiomethyl-3-cephem-4-carboxylic acid prepared as described in Example 8 (yield, 94%).

NMR Spectrum (DMSO-d6-TMS) δ(ppm) : 3.56 (broad singlet, 2H 2-$CH_2$), 3.76 (singlet, 2H, —$CH_2$—CONH—), 4.96 (doublet, 1H, 6-H, J=5.0Hz), 5.63 (double doublet, 1H, 7-H), 8.85 (singlet, 1H, triazole ring proton) and 9.13 (doublet, 1H, —CONH—, J=8Hz).

The antimicrobial activity was follows:

| Test Microorganism | MIC (γ/mg) |
| --- | --- |
| *Escherichia coli* | 25 |
| *Proteus vulgaris* | 100 |
| *Salmonella* | 12.5 |
| *Staphylococcus aureaus* | 0.2 |

While the invention has been described in detail and with reference to specific embodiment thereof, it will be apparent to one skilled in the art that various changes and modifications can be made therein without departing from the spirit and scope thereof.

What is claimed is:

1. A cephalosporin compound represented by the formula (I)

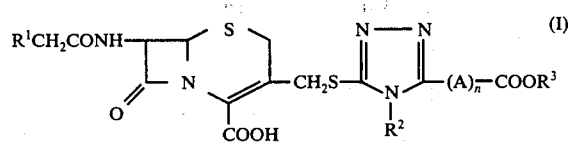

wherein $R^1$ represents a phenyl group, a 2-thienyl group or a phenoxy group; $R^2$ represents a hydrogen atom, an alkyl group having 1 to 4 carbon atoms which may be substituted with a phenyl group, an alkoxy group having 1 to 4 carbon atoms or a halogen atom, or a phenyl group which may be substituted with one or two groups selected from the group consisting of a halogen atom, a nitro group, an alkyl group having 1 to 4 carbon atoms and an alkoxy group having 1 to 4 carbon atoms; $R^3$ represents a hydrogen atom or an alkyl group having 1 to 4 carbon atoms which may be substituted with a monoalkylamino group having 1 to 4 carbon atoms in the alkyl moiety thereof, a dialkylamino group having 1 to 4 carbon atoms in each alkyl moiety thereof, a halogen atom or a phenyl group which may be substituted with one to three groups selected from the group consisting of a halogen atom, a nitro group, an alkyl group having 1 to 4 carbon atoms and an alkoxy group having 1 to 4 carbon atoms; A has up to 15 carbon atoms and, represents a straight or branched chain alkylene group, a straight or branched chain alkenylene group, a straight or branched chain alkadienylene group or a phenylene group, and n is 0 or 1; or the salt thereof.

2. 7-(2-Thienylacetamido)-3-(5-carboxymethyl-1,3,4-triazol-2-yl)thiomethyl-3-cephem-4-carboxylic acid and a salt thereof according to claim 1.

3. 7-(2-Thienylacetamido)-3-[5-(2-carboxyethyl)-1,3,4-triazol-2-yl]thiomethyl-3-cephem-4-carboxylic acid and a salt thereof according to claim 1.

4. 7-(2-Thienylacetamido)-3-[5-(2-carboxyethyl)-1-methyl-1,3,4-triazol-2-yl]thiomethyl-3-cephem-4-carboxylic acid and a salt thereof according to claim 1.

5. 7-(2-Thienylacetamido)-3-[5-(2-carboxyethyl)-1-phenyl-1,3,4-triazol-2-yl]thiomethyl-3-cephem-4-carboxylic acid and a salt thereof according to claim 1.

6. 7-(2-Thienylacetamido)-3-(5-carboxymethyl-1-methyl-1,3,4-triazol-2-yl)thiomethyl-3-cephem-4-carboxylic acid and a salt thereof according to claim 1.

7. 7-(2-Thienylacetamido)-3-(5-carboxy-1,3,4-triazol-2-yl)thiomethyl-3-cephem-4-carboxylic acid and a salt thereof according to claim 1.

8. 7-(2-Thienylacetamido)-3-(5-carboxy-1-methyl-1,3,4-triazol-2-yl)thiomethyl-3-cephem-4-carboxylic acid and a salt thereof according to claim 1.

9. 7-(2-Thienylacetamido)-3-(5-carboxy-1-phenyl-1,3,4-triazol-2-yl)thiomethyl-3-cephem-4-carboxylic acid and a salt thereof according to claim 1.

10. 7-(2-Thienylacetamido)-3-(5-carboxymethyl-1-phenyl-1,3,4-triazol-2-yl)thiomethyl-3-cephem-4-carboxylic acid and a salt thereof according to claim 1.

11. 7-(2-Thienylacetamido)-3-[5-(3-carboxypropyl)-1-methyl-1,3,4-triazol-2-yl]thiomethyl-3-cephem-4-carboxylic acid and a salt thereof according to claim 1.

12. 7-(2-Thienylacetamido)-3-[5-(3-carboxypropyl)-1-phenyl-1,3,4-triazol-3-yl]thiomethyl-3-cephem-4-carboxylic acid and a salt thereof according to claim 1.

13. 7-(2-Thienylacetamido)-3-(5-acryl-1-methyl-1,3,4-triazol-2-yl)thiomethyl-3-cephem-4-carboxylic acid and a salt thereof according to claim 1.

14. 7-(2-Thienylacetamido)-3-(5-acryl-1-phenyl-1,3,4-traizol-2-yl)thiomethyl-3-cephem-4carboxylic acid and a salt thereof to claim 1.

15. 7-(Phenoxyacetamido)-3-(5-carboxymethyl-1,3,4-triazol-2-yl)thiomethyl-3-cephem-4-carboxylic acid and a salt thereof according to claim 1.

16. 7-(Phenoxyacetamido)-3-(5-carboxymethyl-1-methyl-1,3,4-triazol-2-yl)thiomethyl-3-cephem-4-carboxylic acid and a salt thereof according to claim 1.

17. 7-(Phenoxyacetamido)-3-(5-carboxyethyl-1,3,4-triazol-2-yl)thiomethyl-3-cephem-4-carboxylic acid and a salt thereof according to claim 1.

18. 7-(Phenoxyacetamido)-3-(5-carboxyethyl-1-methyl-1,3,4-triazol-2-yl)thiomethyl-3-cephem-4-carboxylic acid and a salt thereof according to claim 1.

19. 7-(Phenylacetamido)-3-(5-carboxymethyl-1,3,4-triazol-2-yl)thiomethyl-3-cephem-4-carboxylic acid and a salt thereof according to claim 1.

20. 7-(Phenylacetamido)-3-(5-carboxymethyl-1-methyl-1,3,4-triazol-2-yl)thiomethyl-3-cephem-4-carboxylic acid and a salt thereof according to claim 1.

21. 7-(Phenylacetamido)-3-(5-carboxyethyl-1,3,4-triazol-2-yl)thiomethyl-3-cephem-4-carboxylic acid and a salt thereof according to claim 1.

22. 7-(Phenylacetamido)-3-(5-carboxyethyl-1-methyl-1,3,4-triazol-2-yl)thiomethyl-3-cephem-4-carboxylic acid and a salt thereof according to claim 1.

23. A process for preparing a cephalosporin compound represented by the formula (I')

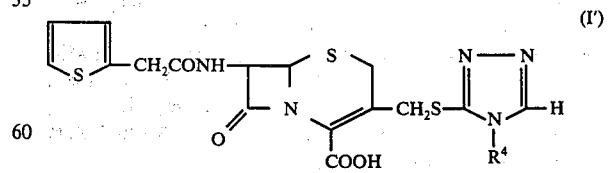

wherein $R^4$ represents a straight or branched chain alkyl group having 1 to 4 carbon atoms, which comprises decarboxylating a cephalosporin compound represented by the formula (I), said decarboxylation being carried out (A) in a solvent selected from the group consisting of water, an organic solvent and mixtures thereof at a pH of about 1 to 6 and at a temperature ranging from room temperature to 100° C, (B) by employing an active carbon or palladium-on-active carbon catalyst or (C) by allowing the free carboxylic acid compound to stand as a solid under reduced or normal pressure,

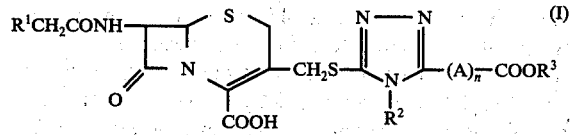

wherein $n$ is 0; $R^1$ represents a 2-thienyl group; $R^2$ represents an alkyl group having 1 to 4 carbon atoms; $R^3$ represents a hydrogen atom or an alkyl group having 1 to 4 carbon atoms which may be substituted with a monoalkylamino group having 1 to 4 carbon atoms in the alkyl moiety thereof, a dialkylamino group having 1 to 4 carbon atoms in each alkyl moiety thereof, a halogen atom or a phenyl group which may be substituted with one to three groups selected from the group consisting of a halogen atom, a nitro group, an alkyl group having 1 to 4 carbon atoms and an alkoxy group having 1 to 4 carbon atoms; and A represents a straight or branched chain alkylene group, a straight chain or branched chain alkenylene group, a straight chain or branched chain alkadienylene group or a phenylene group.

24. A process for preparing a cephalosporin compound represented by the formula (I')

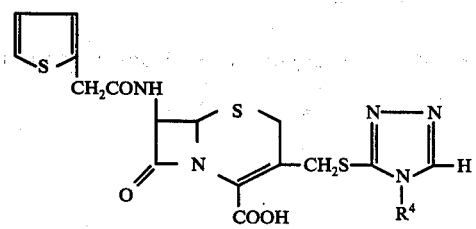

comprising reacting a cephalosporin compound represented by the formula (II)

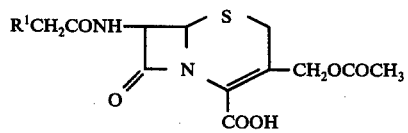

with a 1,3,4-triazole compound represented by the formula (III),

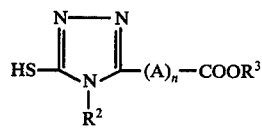

or the corresponding mercaptide compound thereof, to produce the cephalosporin compound of the formula (I)

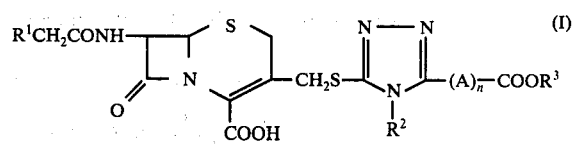

wherein in the above formulae I, $R_1$ represents a 2-thienyl group, II, III and I', $R^2$ represents a hydrogen atom, an alkyl group having 1 to 4 carbon atoms which may be substituted with a phenyl group, $R^3$ represents a hydrogen atom or an alkyl group having 1 to 4 carbon atoms which may be substituted with a monoalkylamino group having 1 to 4 carbon atoms in the alkyl moiety thereof, a dialkylamino group having 1 to 4 carbon atoms in each alkyl moiety thereof, a halogen atom or a phenyl group which may be substituted with one to three selected from the group consisting of a halogen atom, a nitro group, an alkyl group having 1 to 4 carbon atoms and an alkoxy group having 1 to 4 carbon atoms; $R^4$ represents an alkyl group having 1 to 4 carbon atoms; A has up to 15 carbon atoms and represents a straight or branched chain alkylene group, a straigth chain or branched chain alkenylene group, a straight chain or branched chain alkadienylene group or a phenylene group and $n$ is 0; and decarboxylating the resulting compounds to cleave the —$COOR^3$ group to form the corresponding cephalosporin compound of the formula (I'), said decarboxylation being carried out (A) in a solvent selected from the group consisting of water, an organic solvent and mixtures thereof at a pH of about 1 to 6 and at a temperature ranging from room temperature to 100° C, (B) by employing an active carbon or palladium-on-active carbon catalyst or (C) by allowing the free carboxylic acid compound to stand as a solid under reduced or normal pressure, and if necessary, converting the compound of the formula (I') to the salt thereof.

25. A process for preparing a cephalosporin compound represented by the formula (I')

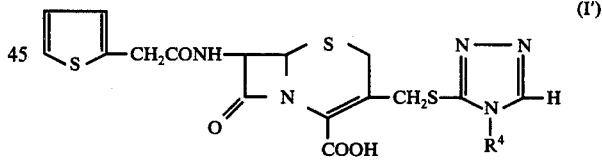

comprising reacting a 7-aminocephalosporanic acid represented by the formula (IV)

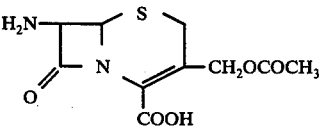

or the salt thereof, with a 1,3,4-triazole compound represented by the formula (III)

or the corresponding mercaptide compound thereof to produce a compound represented by the formula (V),

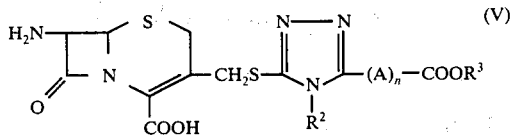

or the salt thereof, or a derivative thereof having a blocked carboxyl group, acylating the compound of the formula (V) with an active derivative of a carboxylic acid derivative represented by the formula (VI)

$$R^1-CH_2COOH \qquad (VI)$$

to produce the cephalosporin compound of the formula (I)

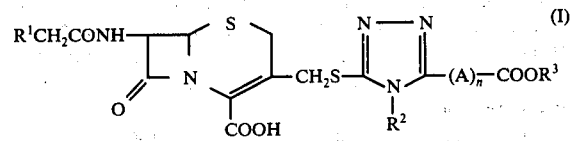

wherein in the above formula $R^1$ represents a 2-thienyl group; $R^2$ represents an alkyl group having 1 to 4 carbon atoms which may be substituted with a phenyl group; $R^3$ represents a hydrogen atom or an alkyl group having 1 to 4 carbon atoms which may be substituted with a monoalkylamino group having 1 to 4 carbon atoms in the alkyl moiety thereof, a dialkylamino group having 1 to 4 carbon atoms in each alkyl moiety thereof, a halogen atom or a phenyl group which may be subsituted with one to three groups selected from the group consisting of a halogen atom, a nitro group, an alkyl group having 1 to 4 carbon atoms and an alkoxy group having 1 to 4 carbon atoms; $R^4$ represents an alkyl group having 1 to 4 carbon atoms; A has up to 15 carbon atoms and represents a straight or branched chain alkylene group, a straight chain or branched chain alkenylene group, a straight chain or branched chain alkadienylene group or a phenylene group and $n$ is 0; or the salt thereof; and decarboxylating the compounds of the formula (I) to cleave the $-COOR^3$ group to form the corresponding cephalosporin compound of the formula (I'), said decarboxylation being carried out (A) in a solvent selected from the group consisting of water, an organic solvent and mixtures thereof at a pH of about 1 to 6 and at a temperature ranging from room temperature to 100° C, (B) by employing an active carbon or palladium-on-active carbon catalyst or (C) by allowing the free carboxylic acid compound to stand as a solid under reduced or normal pressure, and if necessary, converting the compound of formula (I') to the salt thereof, or decarboxylating the resulting compound of the formula (V) employing the above decarboxlation conditions to cleave the $-COOR^3$ group to form the corresponding compounds of the formula (V')

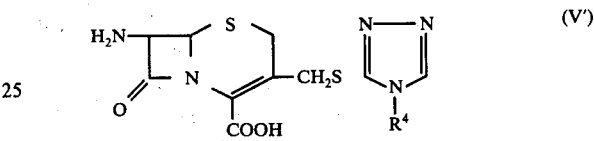

wherein $R^4$ is as defined above, and acylating the resulting compound of the formula (V') with an active derivative of the 2-thienylmethyl carboxylic acid represented by the formula (VI)

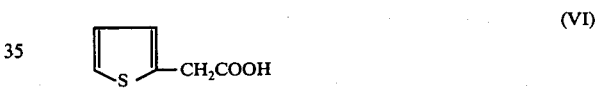

to form the cephalosporin compounds of the formula (I').

* * * * *